United States Patent [19]

Serno

[11] Patent Number: 4,711,902

[45] Date of Patent: Dec. 8, 1987

[54] MEDICAMENT FORMULATION

[75] Inventor: Peter Serno, Cologne, Fed. Rep. of Germany

[73] Assignee: Bayer Aktiengesellschaft, Leverkusen, Fed. Rep. of Germany

[21] Appl. No.: 662,469

[22] Filed: Oct. 18, 1984

[30] Foreign Application Priority Data

Oct. 28, 1983 [DE] Fed. Rep. of Germany ....... 3339236

[51] Int. Cl.$^4$ .............. A61K 31/44; A61K 31/41; A61K 31/415; A61K 31/24
[52] U.S. Cl. .................. 514/356; 514/359; 514/404; 514/538; 514/937
[58] Field of Search ............. 514/356, 359, 538, 404

[56] References Cited

U.S. PATENT DOCUMENTS

| 3,764,683 | 10/1973 | Bosserf et al. | 514/356 |
|---|---|---|---|
| 4,237,137 | 12/1980 | Tacke et al. | 514/256 |
| 4,264,611 | 4/1981 | Berntsson et al. | 514/356 |

FOREIGN PATENT DOCUMENTS

| 65820 | 6/1981 | Japan | 514/356 |

*Primary Examiner*—J. R. Brown
*Assistant Examiner*—John W. Rollins, Jr.
*Attorney, Agent, or Firm*—Sprung Horn Kramer & Woods

[57] ABSTRACT

A medicament formulation of intravenous injection comprising a medicinally active compound, a lipid phase, an emulsifier and water, the lipid phase being present in up to about 30% by weight, the emulsifier being present in about 0.1 to 10% by weight, and water being present up to 100%, the lipid phase containing up to about 50% by weight of a sparingly soluble medicinally active compound, and consisting essentially of (a) at least one ester principally of at least one medium chain-length fatty acid, or
(b) a mixture of at least one ester principally of at least one medium chain-length fatty acid with at least one vegetable or animal oil, the mixture containing at least 10% by weight of the ester principally of the medium chain-length fatty acid, or
(c) at least one ester principally of at least one medium chain-length fatty acid, at least one vegetable or animal oil, or a mixture thereof, in combination with 0.3 to 200% by weight of benzyl alcohol based on the content of lipid or oil. A greater amount of medicinal agent can be administered in a reduced total volume of injectable liquid.

24 Claims, No Drawings

MEDICAMENT FORMULATION

The invention relates to a medicament formulation for intravenous injection, and to a process for its preparation.

It is known that medicinal active compounds can be administered intravenously only in the dissolved form. Active compounds which dissolve in water only slightly or not at all have to be induced to dissolve by solubilizing means.

The means hitherto disclosed, such as the addition of organic solvents, have proved to be unsatisfactory since, as a consequence of these additions, unfavorable physiological side effects, such as injection pain, thrombophlebitis, histaminoid reactions, bronchospasms or cardiovascular collapse, may occur.

According to DE-AS (German Published Specification) No. 1,792,410, these disadvantages can be avoided by administering the sparingly soluble medicaments in the form of a lipid emulsion, consisting of a vegetable or animal oil, in particular soy bean oil, which is dispersed in water with the addition of emulsifiers and of agents to produce isotonicity.

However, this process presupposes that the sparingly soluble medicaments dissolve in sufficient amounts in vegetable or animal oils, in particular soy bean oil, but in most cases this is not guaranteed.

The low solvent power for medicinal active compounds which are sparingly soluble in water leads to the use of additions of large amounts which are undesired per se. Due to the addition of these large amounts, a large amount of liquid is, for a set amount of active compound, unavoidably introduced into the body. Due to the high lipid content associated with the administration, there is likewise introduction of high caloric energy which is undesired.

It has now been found that a considerable increase in the solubility in lipid emulsions of medicinal active compounds which are sparingly soluble in water can be achieved by the following means:

(1) Use of esters principally of medium chain-length fatty acids as components in the lipid phase in the emulsion, or
(2) addition of benzyl alcohol to the lipid emulsion, or
(3) combined use of esters principally of medium chain-length fatty acids and of benzyl alcohol.

Thus the invention relates to a medicament formulation for intravenous injection containing medicinal active compound, lipid phase, emulsifier and water, the lipid phase being present in amounts up to 30% by weight, preferably 5 to 20% by weight, the emulsifier being present in amounts of 0.1 to 10% by weight, and water being present up to 100%, and the lipid phase containing up to 50% by weight of a sparingly soluble medicinal active compound, and consisting of
(a) esters principally of medium chain-length fatty acids, or
(b) mixtures of esters principally of medium chain-length fatty acids with vegetable or animal oils containing at least 10% by weight, preferably at least 30% by weight, of esters principally of medium chain-length fatty acids, or
(c) esters principally of medium chain-length fatty acids, vegetable or animal oils, or their mixtures in combination with 0.3 to 200% by weight of benzyl alcohol based on the content of lipid or oil.

In addition to water for injections, the aqueous phase can contain up to 10% by weight of customary agents for producing isotonicity, such as glycerol or xylitol.

Suitable emulsifiers are the physiologically tolerated emulsifiers, such as phospholipids, polyoxyethylene/polyoxypropylene copolymers, polyethylene glycol sorbitan fatty acid esters, polyethylene glycol fatty acid esters, cholesterol, cholesterol esters and sodium salts of fatty acids.

Esters principally of medium chain-length fatty acids which may be mentioned are:

monoesters, diesters or polyesters of monohydric or polyhydric, preferably monohydric to trihydric, saturated $C_1$–$C_{18}$, preferably $C_2$–$C_6$, aliphatic alcohols, such as, for example, methanol, ethanol, ethanediol, propanol, propanediol, propanetriol, butanol, butane(di-, tri- or tetra-)ol, pentanol, pentane(di-, tri- or penta-)ol, hexanol, hexane(di-, tri-, tetra-, penta- or hexa-)ol, octanol, decanol, dodecanol, tetradecanol, hexadecanol and octadecanol.

Glycerol and propylene 1,2-glycol may be mentioned as preferred.

The acid component used in the esters are (based on the total weight as acids) 55 to 100% by weight monobasic or dibasic, saturated or unsaturated $C_6$–$C_{12}$, preferably $C_8$–$C_{10}$, fatty acids (=medium chain-length fatty acids), and 0 to 45% by weight monobasic, dibasic or polybasic, saturated or unsaturated $C_1$–$C_5$ or $C_{13}$–$C_{22}$ carboxylic acids.

Examples of medium chain-length fatty acids of these types are:

hexanoic acid, hexenoic acid, hexadienoic acid, octanoic acid, octenoic acid, octa(di- or tri-)enoic acid, decanoic acid, decenoic acid, deca(di-, tri- or tetra-)enoic acid, dodecanoic acid, dodeca(di-, tri-, tetra- or penta-)-enoic acid, and all analogous dioic acids.

Examples of carboxylic acids of this type are:

formic acid, acetic acid, propionic acid, butyric acid, valeric acid, myristic acid, palmitic acid, stearic acid, arachidic acid, behenic acid, butenoic acid, hexadecenoic acid, oleic acid, docosenoic acid, linoleic acid, linolenic acid, arachidonic acid, malonic acid, succinic acid, glutaric acid, suberic acid, butenedioic acid, glycolic acid, lactic acid, ricinoleic acid, malic acid, tartaric acid and citric acid.

Examples of vegetable or animal oils which may be mentioned are soy bean oil, safflower oil and/or cottonseed oil.

Examples of medicinal active compounds which are sparingly soluble in water and which may be listed are: corticoids, such as cortisone acetate, hydrocortisone, dexamethasone and triamcinolone acetonide, benzodiazepines, such as diazepam and flunitrazepam, antiepileptics, such as diphenylhydantoin and clonazepam, chemotherapeutics, such as nitrofurantoin, sulfamethoxazole and trimethoprim, antimycotics, such as griseofulvin and amphotericin B, cardiac glycosides, such as digoxin and deslanoside, ergot alkaloids, such as dihydroergotamine mesilate and ergotamine tartrate, cytostatics, such as melphalan, barbiturates, such as pentobarbitone sodium, and lipid-soluble vitamins, such as vitamin A, $B_2$, $B_6$ $B_{12}$, E or $K_1$.

Very particularly important are the dihydropyridine compounds, in particular those having the following general formula (I)

in which
R$_1$ denotes C$_1$-C$_4$-alkyl, optionally substituted by C$_1$-C$_3$-alkoxy,
R$_2$ denotes C$_1$-C$_{10}$-alkyl, optionally substituted by C$_1$-C$_3$-alkoxy, trifluoromethyl or N-methyl-N-benzylamine,
R$_3$ denotes C$_1$-C$_4$-alkyl, cyano or hydroxymethyl, and
X denotes 2- or 3-nitro, 2,3-dichloro or 2,3-=N—O—N= completing a ring.

Especially preferred are the compounds of the following table:

TABLE

| No. | X | R$^1$ | R$^2$ | R$^3$ | Generic name |
|---|---|---|---|---|---|
| 1 | 2-NO$_2$ | CH$_3$ | CH$_3$ | CH$_3$ | Nifedipine |
| 2 | 3-NO$_2$ | nPrOCH$_2$CH$_2$ | nPrOCH$_2$CH$_2$ | CH$_3$ | Niludipine |
| 3 | 3-NO$_2$ | C$_2$H$_5$ | CH$_3$ | CH$_3$ | Nitrendipine |
| 4 | 2-NO$_2$ | CH$_3$ | (CH$_3$)$_2$CHCH$_2$ | CH$_3$ | Nisoldipine |
| 5 | 3-NO$_2$ | CH(CH$_3$)$_2$ | (CH$_2$)$_2$—O—CH$_3$ | CH$_3$ | Nimodipine |
| 6 | 3-NO$_2$ | C$_2$H$_5$ | C$_{10}$H$_{21}$(n) | CH$_3$ | |
| 7 | 2-Cl | CH$_3$ | CH$_2$—CF$_3$ | CH$_3$ | |
| 8 | 2-Cl | C$_2$H$_5$ | CH$_2$—CF$_3$ | CH$_3$ | |
| 9 | 3-NO$_2$ | CH(CH$_3$)$_2$ | n-PrO—CH$_2$CH$_2$ | CH$_3$ | |
| 10 | 3-NO$_2$ | CH$_3$ | C$_6$H$_5$CH$_2$N(CH$_3$)CH$_2$CH$_2$ | CH$_3$ | Nicardipin |
| 11 | 2,3-Cl$_2$ | C$_2$H$_5$ | CH$_3$ | CH$_3$ | Felodipin |
| 12 | 2,3=N—O—N= | C$_2$H$_5$ | C$_2$H$_5$ | CH$_3$ | |
| 13 | 2,3=N—O—N= | CH$_3$ | CH(CH$_3$)$_2$ | CH$_3$ | |
| 14 | 3-NO$_2$ | C$_2$H$_5$ | C$_2$H$_5$ | CH$_2$OH | |
| 15 | 3-NO$_2$ | CH$_3$ | CH$_3$ | CN | | n-Pr = n-Propyl

The following may be particularly mentioned: nifedipine, nimodipine, nitrendipine and nisoldipine.

Likewise important are imidazole derivatives of the formula where
R$_1$ denotes, where appropriate, araylalkyl chains substituted by chlorine, hydroxyl or arylalkoxy.

Compounds having the following substituents are very particularly suitable:

R$_1$ = —CH$_2$—CH—O—CH$_2$ such as miconazole econazole isoconazole or 2 × Cl or 2 × Cl R$_1$ = —CH$_2$ ketoconazole R$_1$ = clotrimazole R$_1$ = —CH— bifonazole In addition, muzolimine and propanidide.

The medicament formulation according to the invention is advantageously prepared in a two-step process, initially a pre-emulsification being carried out, and this being followed by a homogenization process.

The pre-emulsion is prepared by vigorously mixing amounts of the lipophilic constituents, such as the esters principally of medium chain-length fatty acids, the vegetable or animal oils, the medicinal active compound and, where appropriate, benzyl alcohol, in the appropriate ratios, at temperatures up to 75° C. until a homogeneous solution or dispersion is produced, and then vigorously mixing, and, where appropriate, subjecting to a preliminary reduction in size in a vortex chamber, this mixture with water which, where appropriate, contains the agent for producing isotonicity, the emulsifier being introduced either into the lipophilic phase or the aqueous phase, or in appropriate part amounts into both phases. The pH of the pre-emulsion is adjusted to a physiological figure which is optimal for emulsification, for example 7.6.

This pre-emulsion is then homogenized until an emulsion having a mean diameter of the lipid droplets of less than 2 μm, in particular less than 1 μm, is produced.

The homogenization can be carried out by, for example, high-pressure homogenizers under pressures up to 1,000 bar, preferably 400 bar or by ultrasonic equipment.

As already mentioned, the advantage of the medicament formulation according to the invention compared with conventional intravenous formulations of medicaments which are sparingly soluble in water comprises, inter alia, the fact that lower amounts of lipid are required to dissolve the medicament which is sparingly soluble in water. Due to the lower amounts of lipid, the volume administered can be reduced to such an extent that medicament therapy of humans becomes possible. The numerous disadvantages of an excessive intravenous intake of lipids, such as hyperalimentation, anaemia, effects on the blood coagulation system, and impairment of liver function, can be avoided.

As is clear from Table 1 below, the medicinal active compounds which were investigated as examples show, in the emulsions of some emulsions of mixed esters of various medium chain-length fatty acids which were selected as examples, solubilities which ranged from about twice to more than forty times those in soy bean oil emulsions.

glycerol monoesters of caprylic acid (60%) and capric acid (40%)

Ester mixture D: 50% soy bean oil and 50% glycerol triesters of caprylic acid (70%) and capric acid (30%)

The improvement in the solubility of the medicinal active compound in emulsions of soy bean oil and/or esters of principally medium chain-length fatty acids which can be achieved by also using benzyl alcohol is clear from Table 2. As can be seen from the data listed, a concentration of as little as 5% by weight of benzyl alcohol in parenteral lipid emulsions leads to an increase in the solubility of the medicament by a factor of 2.8 to 4.5.

TABLE 2

Increase in the solubility of a medicament, which is sparingly soluble in water, in parenteral lipid emulsions by the addition of benzyl alcohol (figures at room temperature, lipid content of the emulsion 20%)

| Benzyl alcohol content in the emulsion (% W/W) | Solubility of nimodipine in the emulsion of esters principally of medium chain-length fatty acids* | Solubility of nimodipine in soy bean oil emulsion |
|---|---|---|
| 0% | 0.16% | 0.04% |
| 2% | 0.22% | 0.08% |
| 4% | 0.36% | 0.16% |
| 5% | 0.46% | 0.18% |

*triglycerides of medium chain-length fatty acids comprising 70% caprylic acid and 30% capric acid were used.

Further advantages of using esters principally of medium chain-length fatty acids and/or benzyl alcohol comprise the fact that, after homogenization, smaller droplet diameters, and thus improved stability of the emulsion, are achieved. Moreover, when esters principally of saturated medium chain-length fatty acids are used, there is an improvement in the stability with respect to lipid oxidation.

The preparation of the medicament formulations may be illustrated by the examples which follow:

EXAMPLE 1

TABLE 1

Comparison of the solubilities of medicaments, which are sparingly soluble in water, in emulsions of soy oil and various esters principally of medium chain-length fatty acids
(Lipid content of the emulsions 20% by weight, figures at room temperature)

| Lipid phase in the emulsion | Solubility of the medicament in the emulsion % (W/W) | | | | | |
|---|---|---|---|---|---|---|
| | Nifedipine | Nimodipine | Nitrendipine | Nisoldipine | Muzolimine | Propanidide |
| Ester mixture A principally of medium chain-length fatty acids | 0.08% | 0.16% | 0.08% | 0.14% | 0.06% | infinitely miscible |
| Ester mixture B principally of medium chain-length fatty acids | 0.10% | 0.26% | 0.12% | 0.18% | 0.06% | infinitely miscible |
| Ester mixture C principally of medium chain-length fatty acids | 0.10% | 0.50% | 0.14% | 0.20% | 0.32% | infinitely miscible |
| Ester mixture D | 0.04% | 0.08% | 0.05% | 0.08% | 0.02% | |
| Soy bean oil | 0.02% | 0.04% | 0.03% | 0.04% | 0.01% | 2.80% |

Ester mixture A: a glycerol triesters of caprylic acid (70%) and capric acid (30%)

Ester mixture B: propylene glycol diesters of caprylic acid (75%) and capric acid (25%)

Ester mixture C: 75% glycerol triesters of caprylic acid (70%) and capric acid (30%) 12.5% glycerol diesters of caprylic acid (60%) and capric acid (40%) 12.5%

24.000 g of purified egg-yolk phosphatides are homogeneously dispersed, at 60° to 70° C., in a mixture of 50.000 g of purified soy bean oil for injections and 50.000 g of glycerol triesters of medium chain-length fatty acids, of fatty acid composition 60% by weight caprylic acid and 40% by weight capric acid. 0.100 g of nifedipine is added to this mixture, protected from light. After stirring in 7.500 g of glycerol and 292.500 g of water for injection, a pre-emulsion is produced and, after adjusting the pH to 8.2, this is homogenized by passing through a commercial high-pressure homogenizer at 400 bar 5 times. The extremely fine emulsion produced is, at 20° C., made to a volume of 1 liter with an aqueous phase comprising 975.000 g of water for injections and 25.000 g of glycerol, and is filtered and dispensed into lightproof 50 ml injection vials under an atmosphere of nitrogen.

EXAMPLE 2

6.000 g of purified soy bean phosphatides are dissolved in a mixture of 50.000 g of purified soy bean oil for injections and 50.000 g of benzyl alcohol at 50° C. 0.100 g of nisoldipine is dissolved in this solution, protected from light. After stirring in 150.000 g of water for injections, a pre-emulsion is produced and, after adjusting the pH to 7.6, this is homogenized as described in Example 1. After making up to 1 liter at 20° C. with water for injections, the mixture is dispensed into lightproof 2 ml ampules, protected from light and under an atmosphere of nitrogen.

EXAMPLE 3

15.000 g of purified soy bean phosphatides are dissolved in a mixture of 200 g of glycerol triesters of caprylic acid (50% by weight), capric acid (34% by weight) and succinic acid (16% by weight) and 10.000 g of benzyl alcohol at 50° C. 0.500 g of nitrendipine is dissolved in this solution, protected from light. After stirring in 12.000 g of glycerol and 588.000 g of water, a pre-emulsion is produced, and this is homogenized as described in Example 1. After making up to 1 liter at 20° C. with an aqueous phase comprising 980 g of water for injections and 20 g of glycerol, the mixture is dispensed into lightproof 10 ml ampules, protected from light and under an atmosphere of nitrogen.

EXAMPLE 4

2.000 g of muzolimine are dissolved in a mixture of 150.000 g of glycerol triesters of caprylic acid (70% by weight) and capric acid (30% by weight), 25.000 g of glycerol diesters of caprylic acid (60% by weight) and capric acid (40% by weight) and 25.000 g of glycerol monoesters of caprylic acid (60% by weight) and capric acid (40% by weight). This solution is stirred into 600.00 g of aqueous phase comprising 16.000 g of Pluronic ®F 68 and 584.000 g of water for injections at 50° C. After homogenization as described in Example 1, the mixture is made up to 1 liter at 20° C. with water for injections and dispensed into 10 ml ampules under an atmosphere of nitrogen.

EXAMPLE 5

7.2000 g of purified egg-yolk phosphatides are homogeneously dispersed, at 60°–70° C., in 60.000 g of glycerol triesters of caprylic acid (50% by weight), of capric acid (40% by weight), of linoleic acid (5% by weight) and of caproic and lauric acids (together 5% by weight). 0.400 g of nimodipine is added to this mixture, protected from light. After adding 5.550 g of glycerol and 175.500 g of water for injections and dispersing in a high-speed vortex chamber, a pre-emulsion is produced and this is homogenized as described in Example 1. After making up to 1 liter at 20° C. with an aqueous phase comprising 975.000 g of water for injections and 25.000 g of glycerol, the mixture is dispensed into lightproof 50 ml injection vials, protected from light and under an atmosphere of nitrogen.

EXAMPLE 6

15.000 g of purified soy bean phosphatides are dissolved in a mixture of 200.000 g of propylene glycol diesters of caprylic acid (75% by weight) and capric acid (25% by weight) and 15.000 g of benzyl alcohol at 50° C. 2.000 g of Ketoconazole dissolved in this solution. After stirring in 14.000 g of glycerol and 586.000 g of water for injections, a pre-emulsion is produced, and this is homogenized as described in Example 1. After making up to 1 liter at 20° C. with water for injections, the mixture is dispensed into 10 ml ampules under an atmosphere of nitrogen.

EXAMPLE 7

7.500 g of purified soy bean phosphatides are dissolved in 100.000 g of glycerol triesters of caprylic acid (60% by weight) and capric acid (40% by weight) at 60°–70° C. 50.000 g of propanidide are dissolved in this solution. After stirring in 15.000 g of xylitol and 285.000 g of water for injections, a pre-emulsion is produced, and this is homogenized as described in Example 1. After making up to 1 liter at 20° C. with an aqueous phase comprising 950.000 g of water and 50.000 g of xylitol, the mixture is dispensed into 10 ml ampules under an atmosphere of nitrogen.

It will be understood that the specification and examples are illustrative but not limitative of the present invention and that other embodiments within the spirit and scope of the invention will suggest themselves to those skilled in the art.

What is claimed is:

1. A medicament formulation in the form of a lipid emulsion for intravenous injection comprising a medicinally active compound, a lipid phase, a physiologically tolerated emulsifier and water, the lipid phase being present in an amount of 5 to 20% by weight, the emulsifier being present in about 0.1 to 10% by weight, and water being present up to 100%, the lipid phase containing up to about 50% by weight of a sparingly soluble medicinally active compound, and an ester component said ester component being at least one ester of at least one $C_6$ to $C_{12}$ fatty acid.

2. A formulation according to claim 1, wherein the proportion of the ester of a medium chain-length fatty acid is at least about 30% by weight of the lipid phase.

3. A formulation according to claim 1, wherein the ester of a medium chain-length fatty acid is selected from the group consisting of a monoester of a monohydric saturated alphatic $C_1$–$C_{18}$ alcohol, a monoester of a polyhydric saturated aliphatic $C_1$–$C_{18}$ alcohol, a diester of a monohydric saturated aliphatic $C_1$–$C_{18}$ alcohol, a diester of a polyhydric saturated aliphatic $C_1$–$C_{18}$ alcohol, a polyester of a monohydric saturated aliphatic $C_1$–$C_{18}$ alcohol, and a polyester of a polyhydric saturated aliphatic $C_1$–$C_{18}$ alcohol with 55 to 100% by weight of at least one monobasic or dibasic, saturated or unsaturated $C_6$–$C_{12}$ fatty acid and 0 to 45% by weight of at least one monobasic, dibasic or polybasic, saturated or unsaturated $C_1$–$C_5$ or $C_{13}$–$C_{22}$ carboxylic acid.

4. A formulation according to claim 3, wherein the alcohol component of the ester of a medium chain-length fatty acid is a monohydric to trihydric, aliphatic $C_2$–$C_6$ alcohol.

5. A formulation according to claim 3, wherein the $C_6-C_{12}$ fatty acid is selected from the group consisting of hexanoic acid, hexenoic acid, hexadienoic acid, octanoic acid, octenoic acid, octadienoic acid, octatrienoic acid, decanoic acid, decenoic acid, decadienoic acid, decatrienoic acid, decatetraenoic acid, dodecanoic acid, dodecadienoic acid, dodecatrienoic acid, dodecatetraenoic acid and dodecapentaenoic acid.

6. A formulation according to claim 3, wherein the carboxylic acid is selected from the group consisting of formic acid, acetic acid, propionic acid, butyric acid, valeric acid, myristic acid, palmitic acid, stearic acid, arachidic acid, behenic acid, butenoic acid, hexadecenoic acid, oleic acid, docosenoic acid, linoleic acid, linolenic acid, arachidonic acid, malonic acid, succinic acid, glutaric acid, suberic acid, butenedioic acid, glycolic acid, lactic acid, ricinoleic acid, malic acid, tartaric acid and citric acid.

7. A formulation according to claim 4, wherein the alcohol component is selected from the group consisting of glycerol, propylene 1,2-glycol and mixtures thereof.

8. A formulation according to claim 1, wherein the medicinally active compound is selected from the group consisting of dihydropyridines, pharmaceutically active triazoles, muzolimine and propanidide.

9. A formulation according to claim 1, wherein the medicinally active compound is a dihydropyridine of the formula

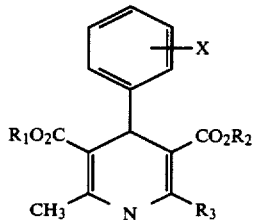

in which
$R_1$ is $C_1-C_4$-alkyl unsubstituted or substituted by $C_1-C_3$-alkoxy,
$R_2$ is $C_1-C_{10}$-alkyl unsubstituted or substituted by $C_1-C_3$-alkoxy, trifluoromethyl or N-methyl-N-benzylamino,
$R_3$ is $C_1-C_4$-alkyl, cyano or hydroxymethyl, and
X is 2- or 3-nitro, 2,3-dichloro or 2,3- =N—O—N= completing a ring.

10. A formulation according to claim 1, wherein the medicinally active compound is nimodipine.

11. A formulation according to claim 1, wherein said emulsifier is selected from the group consisting of phospholipids, polyoxyethylene/polyoxypropylene copolymers, polyethylene glycol sorbitan fatty acid esters, polyethylene glycol fatty acid esters, cholesterol, cholesterol esters and sodium salts of fatty acids.

12. A formulation according to claim 1, wherein the active compound is a dihydropyridine selected from the group consisting of nifedipine, nimodipine, nitrendipine, nisoldipine, niludipine, nicardipin and felodipin.

13. A medicament formulation according to claim 1, wherein the medium-chain length fatty acid is a $C_8$ to $C_{10}$ fatty acid.

14. A medicament formulation according to claim 1, wherein said ester component further comprises 0.3 to 200% by weight of a benzyl alcohol, based on the content of the fatty acid ester.

15. A medicament formulation according to claim 1, wherein said ester component further comprises at least one oil selected from the group consisting of a vegetable oil and an animal oil, the resultant mixture of the ester and the oil containing at least 10% by weight of the ester.

16. A formulation according to claim 15, wherein the vegetable or animal oil comprises soy bean oil, safflower oil, cottonseed oil and mixtures thereof.

17. A medicament formulation according to claim 1, wherein said ester component further comprises at least one oil selected from the group consisting of a vegetable oil and an animal oil and 0.3 to 200% by weight of benzyl alcohol, based on the content of the lipid phase.

18. A medicament formulation in the form of a lipid emulsion for intravenous injection comprising a medicinally active dihydropyridine of the formula

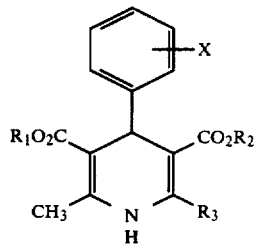

in which
$R_1$ is $C_1-C_4$-alkyl unsubstituted or substituted by $C_1-C_3$-alkoxy,
$R^2$ is $C_1-C_{10}$-alkyl unsubstituted or substituted by $C_1-C_3$-alkoxy, trifluoromethyl or N-methyl-N-benzylamino,
$R_3$ is $C_1-C_4$-alkyl, cyano or hydroxymethyl, and
X is 2- or 3-nitro, 2,3-dichloro or 2,3- =N—O—N= completing a ring, and a lipid phase, said lipid phase being
(a) at least one ester of a monobasic, saturated $C_6-C_{12}$ fatty acid and a saturated aliphatic $C_1-C_{18}$ alcohol, or
(b) a mixture of at least one ester according to (a) and at least one oil selected from the group consisting of a vegetable oil, an animal oil and a mixture thereof.

19. A medicament formulation according to claim 18, wherein the saturated aliphatic $C_1-C_{18}$-alcohol is glycerol.

20. A medicament formulation according to claim 18, wherein the animal oil is soy bean oil.

21. A process for the preparation of a medicament formulation according to claim 1, comprising mixing at a temperature of up to about 75° C. the lipophilic constituents comprising the esters principally of medium chain-length fatty acids and the vegetable or animal oils if present, the medicinally active compound and the benzyl alcohol if present, then vigorously mixing the mixture with water, thereby to form a pre-emulsion, the emulsifier being introduced into either or both of the lipophilic phase or the aqueous phase, and then homogenizing the pre-emulsion until an emulsion having a mean lipid droplet diameter less than about 1 μm is produced.

22. A process according to claim 21, wherein the homogenization is carried out by a high-pressure homogenizer under a pressure up to about 1,000 bar, or by ultrasonic equipment.

23. A process according to claim 21, wherein the water contains an agent for producing isotonicity.

24. A process according to claim 21, wherein the homogenization is carried out by ultrasonic equipment.

* * * * *

UNITED STATES PATENT AND TRADEMARK OFFICE
CERTIFICATE OF CORRECTION

PATENT NO. : 4,711,902
DATED : Dec. 8, 1987
INVENTOR(S) : Serno

It is certified that error appears in the above-identified patent and that said Letters Patent is hereby corrected as shown below:

itle Page, under "U.S.
atent Documents", line 1     Correct spelling of --Bossert--
ol. 7, line 64     Delete "5.550" and substitute --5.500--

Signed and Sealed this

Twenty-eighth Day of June, 1988

Attest:

DONALD J. QUIGG

Attesting Officer     Commissioner of Patents and Trademarks